United States Patent
Kasai (10) Patent No.: US 10,295,471 B2
(45) Date of Patent: May 21, 2019

(54) PLASMA SPECTROSCOPIC ANALYSIS METHOD AND INHIBITOR OF PLASMA EMISSION DERIVED FROM NON-TARGET

(71) Applicant: ARKRAY, Inc., Kyoto (JP)

(72) Inventor: Tokuo Kasai, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 15/724,970

(22) Filed: Oct. 4, 2017

(65) Prior Publication Data

US 2018/0100803 A1  Apr. 12, 2018

(30) Foreign Application Priority Data

Oct. 7, 2016 (JP) .................. 2016-199457
Sep. 21, 2017 (JP) .................. 2017-180832

(51) Int. Cl.

| G01N 21/68 | (2006.01) |
|---|---|
| G01N 33/493 | (2006.01) |
| G01N 21/69 | (2006.01) |
| G01N 1/40 | (2006.01) |

(52) U.S. Cl.
CPC ............ *G01N 21/68* (2013.01); *G01N 21/69* (2013.01); *G01N 33/493* (2013.01); *G01N 2001/4038* (2013.01)

(58) Field of Classification Search
CPC ........ G01N 21/68; G01N 21/69; G01N 21/71; G01N 33/20; G01N 33/493; H01M 4/133
See application file for complete search history.

(56) References Cited

U.S. PATENT DOCUMENTS

| 2013/0321803 A1* | 12/2013 | Kohara | G01N 21/69 356/313 |
|---|---|---|---|
| 2015/0241356 A1* | 8/2015 | Tanaka | G01N 21/69 356/316 |
| 2016/0202187 A1 | 7/2016 | Shiraki et al. | |
| 2017/0222213 A1* | 8/2017 | Hayashi | H01M 4/133 |

FOREIGN PATENT DOCUMENTS

| EP | 2910929 A1 | 8/2015 |
|---|---|---|
| KR | 2016-0087359 A | 7/2016 |
| WO | 2012/120919 A1 | 9/2012 |

OTHER PUBLICATIONS

Extended European Search Report issued in corresponding European Patent Application No. 17194198.2 dated Feb. 20, 2018.

* cited by examiner

*Primary Examiner* — Jamil Ahmed (74) *Attorney, Agent, or Firm* — Morgan, Lewis & Bockius LLP (57) ABSTRACT

A plasma spectroscopic analysis method includes a concentration process of concentrating a target in a sample, in the vicinity of one of a pair of electrodes in the presence of the sample; a plasma generation process of generating plasma in the sample by applying a voltage to the pair of electrodes; and a detection process of detecting emission of the target generated by the plasma, wherein the plasma generation process is performed in the presence of a defoaming agent.

19 Claims, 6 Drawing Sheets

PLASMA SPECTROSCOPIC ANALYSIS METHOD AND INHIBITOR OF PLASMA EMISSION DERIVED FROM NON-TARGET

CROSS-REFERENCE TO RELATED APPLICATIONS

This application claims priority from Japanese Patent Application No. 2016-199457, filed Oct. 7, 2016, and Japanese Patent Application No. 2017-180832, filed Sep. 21, 2017, the disclosures of which are incorporated herein by reference in their entirety.

BACKGROUND

Technical Field

The present disclosure relates to a plasma spectroscopic analysis method and an inhibitor of plasma emission derived from a non-target.

Related Art

As a trace metal element analysis method, there has been known a method of applying a voltage to a sample containing a target metal to generate plasma and detecting the plasma emission (see, for example, International Publication No. 2012/120919).

However, when the sample is subjected to the analysis, other peak waveforms of plasma not derived from the target may be present in addition to the peak waveform of the plasma derived from the target. This causes a problem that, for example, the peak waveform of the plasma derived from the target cannot be correctly caught since the peak waveform of the plasma derived from the target is overlapped with other peak waveforms, whereby the target cannot be accurately analyzed.

SUMMARY OF THE INVENTION

"Other peak waveforms" are considered to be derived from non-targets other than the target included in the sample. As a method of avoiding the influence of non-targets, a sample pretreatment can be considered, which filters a sample through a filter to remove non-targets from the sample.

However, if a pretreatment using a filter is applied to a sample, for example, the concentration of the target in the sample or the like may change.

Thus, the present disclosure provides, for example, a method capable of suppressing plasma emission derived from a non-target without a need for subjecting a sample to a pretreatment by filtration.

In order to solve the above-mentioned problems, a plasma spectroscopic analysis method according to the present disclosure includes: a concentration process of concentrating a target in a sample, in the vicinity of one of a pair of electrodes in the presence of the sample; a plasma generation process of generating plasma in the sample by applying a voltage to the pair of electrodes; and a detection process of detecting emission of the target generated by the plasma, wherein the plasma generation process is performed in the presence of a defoaming agent.

An inhibitor of plasma emission derived from a non-target according to the present disclosure contains a defoaming agent, and is used in the plasma spectroscopic analysis method according to the present disclosure.

The plasma spectroscopic analysis method according to the present disclosure is capable of, for example, suppressing plasma emission derived from a non-target without subjecting a sample to a pretreatment by filtration.

BRIEF DESCRIPTION OF THE DRAWINGS

FIG. 2A and FIG. 2B are graphs showing a spectrum in the vicinity of a peak of emission derived from mercury in Example 1, of which FIG. 2A shows results of Example sample A and Comparative Example sample A of subject A, and FIG. 2B shows results of Example sample B and Comparative Example sample B of subject B.

FIG. 3A and FIG. 3B are graphs showing a spectrum in the vicinity of a peak of emission derived from lead in Example 1, of which FIG. 3A shows results of Example sample A and Comparative Example sample A of subject A, and FIG. 3B shows results of Example sample B and Comparative Example sample B of subject B.

DETAILED DESCRIPTION OF THE INVENTION

<Plasma Spectroscopic Analysis Method>

A plasma spectroscopic analysis method (hereinafter also referred to as an "analysis method") according to the present disclosure includes a concentration process, also referred to herein as a condensing process, of concentrating a target in a sample, in the vicinity of one of a pair of electrodes in the presence of the sample; a plasma generation process of generating plasma in the sample by applying a voltage to the pair of electrodes; and a detection process of detecting emission of the target generated by the plasma, wherein the plasma generation process is performed in the presence of a defoaming agent. Other processes and conditions are not particularly limited.

As a result of earnest research, the inventors have found that, although the mechanism is unknown, plasma emission derived from a non-target can be suppressed by generating plasma in the presence of a defoaming agent. Therefore, for example, in the analysis method according to the present disclosure, by performing the plasma generation process in the presence of the defoaming agent without performing a pretreatment for removing the non-target from the sample by filtration, plasma emission derived from a non-target can be suppressed. As a result, the influence of the plasma emission derived from a non-target is reduced, and therefore, the target can be analyzed with higher accuracy by detecting the plasma emission derived from the target.

In the present disclosure, a mechanism of suppressing plasma emission derived from a non-target by generating the plasma in the presence of the defoaming agent is presumed as follows. By performing a plasma generation process in the presence of a defoaming agent, the amount of bubbles growing around the electrode in the sample becomes relatively small compared to the amount of bubbles in the absence of a defoaming agent. In the concentration process, the target is concentrated in the vicinity of one of a pair of electrodes, while a non-target is dispersed in the sample without being concentrated in the vicinity of the electrode. Therefore, when the amount of bubbles is reduced by the defoaming agent, the amount of the non-target present on the surface of the bubbles is considered to be relatively reduced as compared to the target concentrated in the vicinity of the electrode. As a result, the plasma emission derived from the non-target occurring on the surface of the bubbles due to plasma is also suppressed. It should be noted that the invention is not limited to the above presumption at all.

In the analysis method according to the present disclosure, the defoaming agent is not particularly limited as long as the defoaming agent is generally used as a defoaming agent. Examples of the defoaming agent include an alcohol compound, a surfactant, and a ketone compound.

Examples of the alcohol compound include methanol, ethanol, isopropanol, and butanol. Examples of the surfactant include an oil-based surfactant, an emulsion-based surfactant, and a polyether-based surfactant. Examples of the oil-based surfactant include SN DEFOAMER 777 (trademark). Examples of the emulsion-based surfactant include SN DEFOAMER 388N (trademark). Examples of the polyether-based surfactant include TRITON (trademark) X-100. Examples of the ketone compound include acetone. In the present disclosure, as a defoaming agent, one type of defoaming agent may be used, or two or more types of defoaming agents may be used in combination.

The amount of the defoaming agent added to the sample is not particularly limited. For example, the concentration (v/v) of the defoaming agent in the sample is preferably from 0.025% by volume to 12.5% by volume, more preferably from 0.25% by volume to 10% by volume, and more preferably from 2.5% by volume to 7.5% by volume.

In the analysis method according to the present disclosure, the sample is, for example, a specimen. The specimen may be a liquid specimen or a solid specimen. The specimen may be used as a liquid specimen as it is without being diluted, or a diluted solution obtained by suspending, dispersing, or dissolving the specimen in a medium may be used as a liquid specimen, for example. In a case in which the specimen is solid, it is preferable to use a diluted solution obtained by suspending, dispersing, or dissolving the specimen in a medium as a liquid specimen, for example. The medium is not particularly limited, and examples thereof include water and buffer solutions. Examples of the specimen include a specimen (sample) derived from a living body, a specimen (sample) derived from the environment, a metal, a chemical substance, and a medicinal product. The specimen derived from a living body is not particularly limited, and examples thereof include urine, blood, hair, saliva, sweat, and nail. Examples of the blood specimen include red blood cells, whole blood, serum, and plasma. Examples of the living body include a human, a non-human animal, or a plant. Examples of the non-human animal include mammals excluding human, fish, and shellfish. The specimen derived from the environment is not particularly limited, and examples thereof include food, water, soil, atmospheric air, and air. Examples of the food include fresh food and processed food. Examples of the water include drinking water, groundwater, river water, seawater, and domestic wastewater.

The target is not particularly limited, and examples thereof include a metal and a chemical substance. The metal is not particularly limited, and examples thereof include aluminum (Al), antimony (Sb), arsenic (As), barium (Ba), beryllium (Be), bismuth (Bi), cadmium (Cd), cesium (Cs), gadolinium (Gd), lead (Pb), mercury (Hg), nickel (Ni), palladium (Pd), platinum (Pt), tellurium (Te), thallium (Tl), thorium (Th), tin (Sn), tungsten (W), and uranium (U). Examples of chemical substance include reagents, agricultural chemicals, and cosmetics. One type of target may be used, or two or more types of targets may be used.

In a case in which the target is a metal, the sample may include, for example, a reagent for separating the metal in the specimen. Examples of the reagent include a chelating agent and a masking agent. Examples of the chelating agent include dithizone, tiopronin, meso-2,3-dimercaptosuccinic acid (DMSA), Sodium 2,3-dimercapto-1-propanesulfonate (DMPS), ethylenediaminetetraacetic acid (EDTA), nitrilotriacetic acid (NTA), ethylenediamine-N,N'-disuccinic acid (EDDS), and α-lipoic acid. In the present disclosure, the term "masking" means inactivating the reactivity of an SH group, and this can be achieved by, for example, chemical modification of the SH group. Examples of the masking agent include maleimide, N-methylmaleimide, N-ethylmaleimide, N-phenylmaleimide, maleimidopropionic acid, iodoacetamide, and iodoacetic acid.

The non-target means substances other than the target. Examples of the non-target include a nonmetal such as water, glass, and a rock.

The sample may be, for example, a sample whose pH has been adjusted (hereinafter also referred to as a "pH-adjusted sample"). The pH of the pH-adjusted sample is not particularly limited. The method of adjusting the pH of the sample is not particularly limited, and for example, a pH adjusting reagent such as an alkaline reagent or an acidic reagent can be used.

Examples of the alkaline reagent include an alkali and an aqueous solution thereof. The alkali is not particularly limited, and examples thereof include sodium hydroxide, lithium hydroxide, potassium hydroxide, and ammonia. Examples of the aqueous solution of the alkali include an aqueous solution of an alkali obtained by diluting the alkali with water or a buffer solution. In the aqueous solution of an alkali, the concentration of the alkali is not particularly limited, and is, for example, from 0.01 mol/L to 5 mol/L.

Examples of the acidic reagent include an acid and an aqueous solution thereof. The acid is not particularly limited, and examples thereof include hydrochloric acid, sulfuric acid, acetic acid, boric acid, phosphoric acid, citric acid, malic acid, succinic acid, and nitric acid. Examples of the aqueous solution of the acid include an aqueous solution of an acid obtained by diluting the acid with water or a buffer solution. In the aqueous solution of an acid, the concentration of the acid is not particularly limited, and is, for example, from 0.01 mol/L to 5 mol/L.

The electrode is not particularly limited, and examples thereof include a solid electrode, and specific examples thereof include a rod electrode. The material of the electrode is not particularly limited as long as the material is a solid conductive material, and can be appropriately determined in accordance with, for example, the type of the target. The material of the electrode may be, for example, a nonmetal, a metal, or a mixture thereof. In the case where the material of the electrode contains a nonmetal, the material of the electrode may contain, for example, one type of nonmetal or two or more types of nonmetals. Examples of the nonmetal include carbon. In the case where the material of the electrode contains a metal, the material of the electrode may contain, for example, one type of metal or two or more types of metals. Examples of the metal include gold, platinum, copper, zinc, tin, nickel, palladium, titanium, molybdenum, chromium, and iron. In the case where the material of the electrode contains two or more types of metals, the material of the electrode may be an alloy. Examples of the alloy include brass, steel, INCONEL (trademark), nichrome, and stainless steel. The pair of electrodes may be formed of, for example, the same material or different materials.

The size of the electrode is not particularly limited as long as, for example, the electrode can be in contact with the sample. In the case where the electrode is a rod electrode, the diameter of the electrode is preferably, for example, from 0.02 mm to 50 mm, and more preferably from 0.05 mm to 5 mm. The length of the electrode is preferably, for example, from 0.1 mm to 200 mm, and more preferably from 0.3 mm to 50 mm. The sizes of the pair of electrodes may be the same or different from each other.

The concentration process in the analysis method according to the present disclosure is a process of concentrating a target in a sample in the vicinity of one of a pair of electrodes in the presence of a sample, as described above. Concentrating, also referred to herein as condensing, a target means increasing the concentration of the target. The concentration method is not particularly limited, and for example, by applying a voltage to the pair of electrodes in the presence of the sample, a target in the sample in the vicinity of one of the pair of electrodes can be concentrated. The pair of electrodes is, for example, in contact (wetted) with the sample. In the concentration process, the range of the vicinity of the electrode is not particularly limited, and examples thereof include a range where plasma is generated in the plasma generation process described later. In the present disclosure, a "vicinity" of an electrode also includes, for example, an area on the electrode, that is, an area in contact with the electrode.

In general, the amount of a target per unit volume in the sample may be increased by concentrating the sample to reduce the total volume (total liquid amount) of the sample, as a pretreatment of the sample. On the other hand, according to the method of concentrating the target in the sample in the vicinity of one of a pair of electrodes, for example, by the method of applying a voltage to the pair of electrodes, a target can be locally accumulated in the vicinity of an electrode even if a pretreatment for reducing the total volume of the sample is not performed. According to this method, for example, in the subsequent plasma generation process, plasma emission derived from the concentrated target is generated due to the plasma generated around the electrode around which the target is accumulated, and the target present locally at a high concentration can be efficiently analyzed. According to the concentration process by voltage application, for example, even if the concentration of the target is low in the sample to be used, the sample can be analyzed more easily with higher sensitivity by the analysis method according to the present disclosure.

In the concentration process, for example, a part of the target may be concentrated in the vicinity of the electrode, or the entire target may be concentrated in the vicinity of the electrode.

In the concentration process, it is preferable that the electric charge condition of the electrode is set such that the target is concentrated around the electrode used for detection of the target, i.e., the electrode for plasma generation in the detection process described later. The electric charge condition is not particularly limited. For example, in the case where the target is positively charged, the electric charge condition may be set such that the electrode for plasma generation is negatively charged. In the case where the target is negatively charged, for example, the electric charge condition may be set such that the electrode for plasma generation is positively charged.

Hereinafter, a method of concentrating a target by applying a voltage to a pair of electrodes will be described in detail.

Concentrating of the target can be controlled by, for example, a voltage. Those skilled in the art can appropriately set a voltage, at which the concentration occurs (hereinafter also referred to as a "concentration voltage"). The concentration voltage may be, for example, 1 mV or higher, or 400 mV or higher. The upper limit of the concentration voltage is not particularly limited, and may be, for example, 1000 V or lower. The concentration voltage may be, for example, the same voltage throughout the concentration process or may vary during the concentration process. The concentration voltage may be, for example, a voltage at which no plasma is generated.

The duration of the concentration process is not particularly limited, and can be appropriately set according to the concentration voltage. The duration of the concentration process is preferably, for example, from 0.2 minutes to 40 minutes, and may be from 1 minute to 5 minutes. The voltage may be, for example, continuously or discontinuously applied to the pair of electrodes. Examples of the discontinuous application include pulse application. In the case where the voltage is applied discontinuously, the duration of the concentration process represents the total duration of the concentration process including the duration for which the concentration voltage is applied and the duration for which the concentration voltage is not applied. In the case where the voltage is applied continuously, the duration of the concentration process represents a duration for which the concentration voltage is applied.

In the case where the concentration voltage is applied discontinuously, the total duration for which the concentration voltage is applied (the duration not including the duration for which the concentration voltage is not applied) is not particularly limited, and can be appropriately set in accordance with the concentration voltage. The total duration for which the concentration voltage is applied is preferably, for example, from 0.2 minutes to 40 minutes, more preferably, from 10 minutes to 40 minutes, and may be from 1 minute to 5 minutes.

The voltage may be applied to the electrodes by a voltage application technique. The voltage application technique is not particularly limited as long as, for example, it can apply a voltage between the electrodes. As a known technique, a voltage generator may be used. In the concentration process, a current between the electrodes may be, for example, constant or may fluctuate. The current between the electrodes may preferably be, for example, from 0.01 mA to 200 mA, more preferably from 10 mA to 60 mA, and still more preferably from 10 mA to 40 mA.

In the concentration process, the current between a pair of electrodes while applying a voltage may be, for example, constant. The phrase "the current between a pair of electrodes while applying a voltage is constant" means that the current between a pair of electrodes while applying a voltage is a constant current. In the present disclosure, the phrase "a current is constant" or the phrase "a constant current" includes a case where the current value between the electrodes is substantially constant. The case where the current value is substantially constant means that the current value ($A_c$) between the electrodes is maintained within a range of a set current value ($A_S$)±20% ($0.8 \times A_S \leq A_c \leq 1.2 \times A_S$) even if the current value fluctuates over time from the set current value. For example, "the current is constant" or "the constant current" applies when the current value ($A_c$) between the electrodes is maintained within a range of a set current value±10% ($0.9 \times A_S \leq A_c \leq 1.1 \times A_S$) or within a range of a set current value±5% ($0.95 \times A_S \leq A_c \leq 1.05 \times A_S$). Regarding the set current value, reference can be made, as an example, to the description of the current between the pair of electrodes, described later.

In the case where the voltage application in the concentration process is discontinuous application, and in the case where "the current between the pair of electrodes while applying the voltage is constant", "while applying the voltage" represents a period during which the voltage is applied, and represents a period not including a period during which no voltage is applied.

In the concentration process, a constant current between a pair of electrodes while applying a voltage tends to suppress occurrences of analysis errors when a sample is analyzed. For example, when samples containing the same concentrations of a target (for example, Pb) are analyzed using the method according to the present disclosure, differences (errors) between the measured values of the amount of the target in a sample containing a coexisting substance (for example, EDTA) and in a sample not containing the coexisting substance tend to be suppressed. Specifically, for example, an error tends to be suppressed to be within a range of ±15%, preferably within a range of ±10%, and more preferably within a range of ±5% with respect to a reference value. The reference value may be appropriately determined by a known method.

In the concentration process, in the case where a current between a pair of electrodes while applying a voltage is constant, the current between the pair of electrodes while applying a voltage may be constant throughout the whole duration of the concentration process, or may be constant during a part of the duration of the concentration process. The duration during which the current between the pair of electrodes is constant is preferably 50% or more, more preferably 70% or more, still more preferably 80% or more, particularly preferably 90% or more, and extremely preferably 100%, with respect to the total duration for which the concentration voltage is applied in the concentration process.

In the concentration process, the voltage application to a pair of electrodes is preferably discontinuous application, since, for example, analysis errors can be further suppressed. In a case in which the voltage application to a pair of electrodes is discontinuous application, the concentration process includes, for example, a voltage application period, in which a voltage is applied to a pair of electrodes, and a voltage non-application period, in which a voltage is not applied to a pair of electrodes. In this case, for example, in the voltage application period, the current between the pair of electrodes while applying a voltage may be constant.

In the voltage application period, by applying a voltage to a pair of electrodes, for example, a target in a sample is concentrated in the vicinity of one of the pair of electrodes. In the voltage application period, the electric charge condition of the electrode is preferably set so as to concentrate the target around the electrode for plasma generation in the plasma generation process described later, that is, the electrode used for detection of emission of the target in the detection process described later. In the voltage application period, regarding the voltage applied to the pair of electrodes, reference can be made to the above description of the concentration voltage, as an example. In the voltage application period, the current between a pair of electrodes is preferably, for example, from 0.01 mA to 200 mA, more preferably from 10 mA to 60 mA, and still more preferably from 10 mA to 40 mA. Particularly preferably, the current between a pair of electrodes may be set to 10 mA or 20 mA.

The voltage application period may occur once or may occur more than once. In the case where the voltage application period occurs more than once, the current between the pair of electrodes in one voltage application period is preferably a constant current. Further, in this case, the current values in more than one voltage application periods may either be the same or different, and are preferably the same.

In the voltage non-application period, no voltage is applied to the pair of electrodes. Therefore, in the voltage non-application period, for example, concentrating of the target in the vicinity of at least one of the electrodes does not occur. In the voltage non-application period, the voltage applied to a pair of electrodes is 0 V. In the voltage non-application period, the current between the pair of electrodes may be set at 0 mA. Note that the exemplified values of the voltage and the current applied to a pair of electrodes in the voltage non-application period are, for example, exemplified values of a voltage and a current applied to a pair of electrodes from outside of the electrodes. Therefore, for example, there may be a potential difference between a pair of electrodes based on the material of the electrode, the type of the sample, and the state of the sample, or the like.

The voltage non-application period may occur once or may occur more than once. The voltage non-application period may occur the same number of times as the voltage application period, or may occur a different number of times, and the former is preferable.

The voltage application period and the voltage non-application period may be controlled, for example, by controlling the applied voltage. Examples of the method of controlling the applied voltage include a method of switching an electric circuit between a closed circuit and an open circuit.

In the case where the electric circuit is switched between a closed circuit and an open circuit, for example, a voltage application period and a voltage non-application period alternately occurs by the electric circuit being switched between a closed circuit and an open circuit. The closed circuit corresponds to the voltage application period, and a voltage can be applied to the pair of electrodes by closing the electric circuit. The open circuit corresponds to the voltage non-application period, and no voltage is applied, that is, the voltage is set at 0 volt (V), by opening the electric circuit. The voltage of the closed circuit is the voltage of the voltage application period, that is, the concentration voltage. The voltage of the open circuit, that is, 0 V is the voltage of the voltage non-application period, and no voltage is applied to the pair of electrodes. The voltage of the closed circuit is not particularly limited, and reference can be made to the exemplification of the concentration voltage.

In the concentration process, when a cycle of one voltage application period and one voltage non-application period is defined as a single set, the duration of the single set is not particularly limited. Hereinafter, the duration of a single set is also referred to as an application cycle. The lower limit of the application cycle is preferably, for example, 250 msec or longer, more preferably 1000 msec or longer, and still more preferably 2000 msec or longer. From the viewpoint of further improving analysis sensitivity, the lower limit of the application cycle is particularly preferably 3000 msec or longer. The upper limit of the application cycle is preferably, for example, 600000 msec or shorter, and more preferably 64000 msec or shorter. The range of the application cycle is preferably, for example, from 250 msec to 600000 msec, more preferably from 1000 msec to 600000 msec, and still more preferably from 2000 msec to 600000 msec.

In the concentration process, when a cycle of one voltage application period and one voltage non-application period is defined as a single set, the duration of the voltage non-application period in the duration of a single set is not particularly limited. Hereinafter, the duration of the voltage non-application period is also referred to as a non-application duration. The lower limit of the non-application duration is preferably, for example, 125 msec or longer, more preferably 1000 msec or longer, and still more preferably 1500 msec or longer. The upper limit of the non-application duration is preferably, for example, 300000 msec or shorter, and more preferably 32000 msec or shorter. The range of the non-application duration is preferably, for example, from 125 msec to 300000 msec, more preferably from 1000 msec to 300000 msec, and still more preferably from 1500 msec to 300000 msec.

In the concentration process, when a cycle of one voltage application period and one voltage non-application period is defined as a single set, the ratio of the duration of the voltage application period to the duration of a single set is not particularly limited. Hereinafter, the ratio of the duration of the voltage application period to the duration of a single set is also referred to as Duty. The Duty is also similarly defined in the plasma generation process described later. The lower limit of the Duty is preferably, for example, 1% or more, more preferably 25% or more, and still more preferably 50% or more. The upper limit of the Duty is preferably, for example, less than 100%, more preferably 85% or less, and still more preferably 50% or less. The range of the Duty is preferably, for example, 1% or more and less than 100%, more preferably from 15% to 85%, and still more preferably from 45% to 55%. The Duty is preferably, for example, 50%.

In the concentration process, the number of cycles of the voltage application period and the voltage non-application period is not particularly limited, and is preferably, for example, from 2 to 9600, more preferably from 300 to 9600, and may be from 3 to 5.

Regarding the concentration process, the conditions per one set of the voltage application period and the voltage non-application period are exemplified below; however, the invention is not limited thereto.

Application cycle (duration of a single set): from 250 msec to 600000 msec

Non-application duration: from 125 msec to 300000 msec

Duty: 1% or more and less than 100%

Current in the voltage application period: from 0.01 mA to 200 mA

Current in the voltage non-application period: 0 mA

In the analysis method according to the present disclosure, the plasma generation process is a process of generating plasma in the sample by applying a voltage to a pair of electrodes in the presence of a defoaming agent.

In the analysis method according to the present disclosure, as long as the defoaming agent is present in the plasma generation process, the timing of addition to an analysis system is not particularly limited. The defoaming agent may be preliminary added to the sample, for example, before the concentration process, or may be added to the sample after the concentration process and before the plasma generation process.

The plasma generation process may be performed successively to the concentration process, or may be performed not successively to the concentration process. In the former case, the plasma generation process is performed immediately after the completion of the concentration process. In the latter case, the plasma generation process is performed within a predetermined time after the completion of the concentration process. The predetermined time may be, for example, from 0.001 seconds to 1000 seconds, or from 1 second to 10 seconds after the concentration process.

In the plasma generation process, the phrase "generating plasma" means to substantially generate plasma. Specifically, the phrase "generating plasma" means generating plasma which causes substantially detectable emission in the detection of plasma emission. As a specific example, plasma is considered to be generated when plasma emission can be detected by a plasma emission detector.

Substantial plasma generation may be adjusted by a voltage, for example. Therefore, those skilled in the art can appropriately set a voltage for generating plasma causing substantially detectable emission (hereinafter, also referred to as "plasma voltage"). The plasma voltage may be, for example, 10 V or higher, and preferably 100 V or higher. The upper limit of the plasma voltage is not particularly limited, and may be, for example, 1000 V or less. A voltage at which plasma is generated is, for example, relatively higher than a voltage at which the concentration occurs. Therefore, the plasma voltage is preferably higher than the concentration voltage. The plasma voltage may be constant, and may fluctuate.

The duration of the plasma generation process is not particularly limited, and may be appropriately set in accordance with to the plasma voltage. The duration for which the plasma voltage is applied is preferably, for example, from 0.001 seconds to 0.02 seconds, and more preferably from 0.001 seconds to 0.01 seconds. The voltage may be, for example, continuously or discontinuously applied to the pair of electrodes. Examples of the discontinuous application include pulse application. In the case where the voltage application is discontinuous, the duration of the plasma generation process represents the total duration of the plasma generation process including the duration for which the plasma voltage is applied and the duration for which the plasma voltage is not applied. In the case where the voltage application is continuous, the duration of the plasma generation process represents the duration for which a plasma voltage is applied.

In the case where the application of the plasma voltage is discontinuous, the duration of one application of the plasma voltage is not particularly limited, and may be appropriately set in accordance with to the plasma voltage. The duration of one application of the plasma voltage is preferably, for example, from 0.01 msec to 0.1 msec, and may be from 0.001 seconds to 0.02 seconds, or from 0.001 seconds to 0.01 seconds.

In the case where the application of the plasma voltage is discontinuous, the total duration for which the plasma voltage is applied (the duration not including the time for which the plasma voltage is not applied) is not particularly limited, and may be appropriately set in accordance with to the plasma voltage. The total duration for which the plasma voltage is applied is preferably, for example, from 0.001 seconds to 0.02 seconds, and more preferably from 0.001 seconds to 0.01 seconds.

In the plasma generation process, the electrode for plasma generation may be adjusted by, for example, making the respective areas of contact of the pair of electrodes with a liquid different from each other. Specifically, by making an area of contact with the liquid of one electrode smaller than an area of contact with the liquid of the other electrode, the one electrode can be caused to generate plasma. Therefore, it is preferable that the pair of electrodes is a pair of electrodes whose areas of contact with the sample are different, and that, of the pair of electrodes, the electrode having a smaller area of contact with the sample is an electrode for analyzing a target by plasma generation. In the case where the areas of contact of the pair of electrodes are different from each other, the difference between the areas of contact of the pair of electrodes is preferably, for example, from 0.001 $cm^2$ to 300 $cm^2$, and more preferably from 1 $cm^2$ to 10 $cm^2$. In the present disclosure, the term "area of contact" means an area in contact with the sample. The method of adjusting the areas of contact is not particularly limited, and examples thereof include: a method of immersing the electrodes in a sample such that the lengths of the immersed parts of the electrodes are different from each other; and a method of coating a part of one of the electrodes in contact with the sample with an insulating material. The insulating material is not particularly limited, and examples thereof include resin, silicone, glass, paper, ceramics, and rubber. Examples of the resin include: thermoplastic resins such as polyethylene, polypropylene, polystyrene, polyvinyl chloride, polyethylene terephthalate, polymethacrylate, polyamide, saturated polyester resin, acrylic resin, polybutylene terephthalate (PBT), polyetheretherketone (PEEK), and polymethylpentene (for example, TPX (trademark)); and thermosetting resins such as urea resin, melamine resin, phenol resin, fluorine resin, epoxy resin (e.g., glass epoxy), and unsaturated polyester resin. Examples of the silicone include polydimethylsiloxane.

The voltage may be applied to the electrodes by a voltage application technique. Regarding the voltage application technique, for example, reference can be made to the above description relating to the voltage application technique in the concentration process. In the plasma generation process, a current between a pair of electrodes is preferably set at, for example, from 0.01 mA to 100000 mA, and more preferably from 50 mA to 2000 mA.

In the analysis method according to the present disclosure, the detection process is a process of detecting emission of the target generated by plasma.

In the detection process, emission caused by generated plasma may be detected, for example, continuously or discontinuously. Examples of the detection of the emission include detection of the presence or absence of the emission, detection of the intensity of the emission, detection of a specific wavelength, and detection of a spectrum. Examples of the detection of a specific wavelength include detection of a specific wavelength accompanied with a plasma emission of the target. The method of detecting the emission is not particularly limited, and for example, a known optical measuring instrument such as a charge coupled device (CCD) or a spectroscope may be used.

Since, in the detection process, the detection is performed by detecting emission caused by the plasma generated in the plasma generation process, the detection process is performed, for example, in parallel with the plasma generation process. The detection process may be performed, for example, successively to the concentration process, and may be performed not successively to the concentration process. In the former case, the detection process is performed, for example, in parallel with the plasma generation process immediately after the completion of the concentration process. In the latter case, the detection process is performed, for example, in parallel with the plasma generation process within a predetermined time after the completion of the concentration process. The predetermined time may be, for example, from 0.001 seconds to 1000 seconds, or may be from 1 second to 10 seconds, after the concentration process.

The analysis method according to the present disclosure may further include a calculation process of calculating the concentration of a target in a sample based on the detection result in the detection process. Examples of the detection result include the above-described emission intensity and the like. In the calculation process, the concentration of the target can be calculated, for example, based on the detection result and the correlation between the detection result and the concentration of the target in the sample. The correlation can be obtained, for example, by carrying out detection with regard to standard samples with known concentrations of the target by the analysis method according to the present disclosure, and plotting the detection results and the concentrations of the target in the standard samples. The standard samples are preferably a dilution series of the target. By carrying out the calculation as described above, highly reliable quantification is made possible.

In the analysis method according to the present disclosure, a pair of electrodes may be placed in a container including a light-transmitting section. In this case, in the detection process, the emission is detected by a light receiving section placed such that it can receive the emission of the target through the light-transmitting section. For the descriptions of the container, the light-transmitting section, and the light receiving section or the like, for example, reference can be made to description of the analyzer which may be used in the analysis method according to the present disclosure, which will be described later.

Next, an example of an analyzer used in the analysis method according to the present disclosure will be described with reference to the drawings. In the drawings, the structure of each component may be shown in an simplified form as appropriate for the sake of convenience in illustration. Further, each component may be shown schematically, and the dimension ratio or the like may be different from the actual dimension ratio or the like.

Figure 1A:
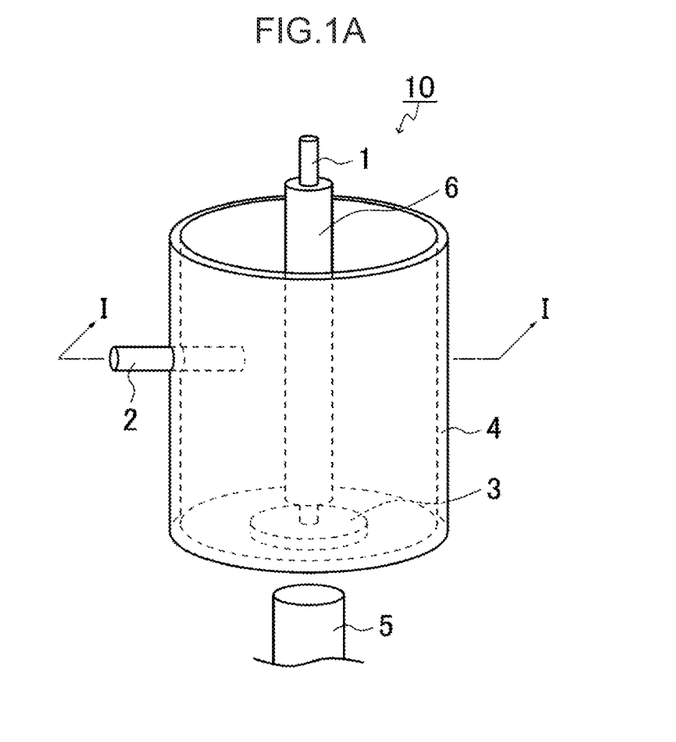
FIG. 1A is a schematic perspective view of a plasma spectroscopic analyzer.
Figure 1B:
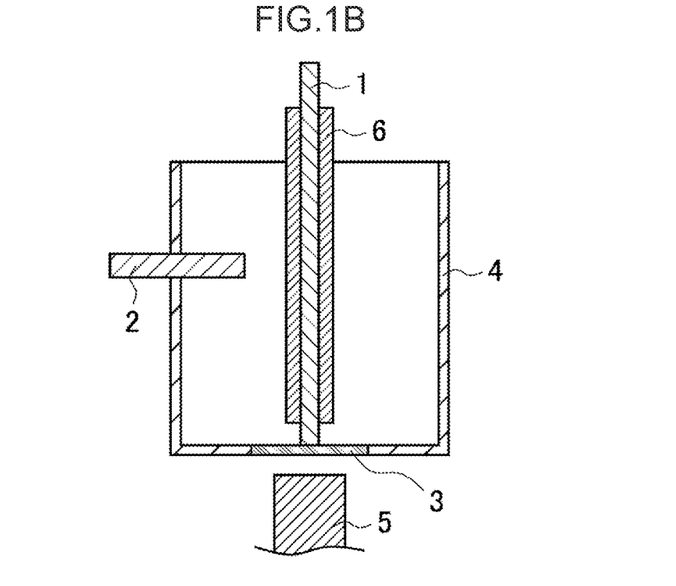
FIG. 1B is a schematic cross-sectional view thereof as seen from an I-I direction of FIG. 1A.

FIG. 1A is a schematic perspective view of a plasma spectroscopic analyzer, and FIG. 1B is a schematic cross-sectional view thereof as seen from an I-I direction in FIG. 1A. As shown in FIGS. 1A and 1B, an analyzer 10 includes a pair of electrodes 1 and 2, a container 4, and a light receiving section 5. The container 4 includes a light-transmitting section 3. The light receiving section 5 is placed outside the container 4 such that it can receive plasma emission, derived from a target, by applying a voltage to the pair of electrodes 1 and 2, through the light-transmitting section 3. The electrode 1 is placed in a direction perpendicular to the bottom surface of the container 4, and one end of the electrode 1 is in contact with the light-transmitting section 3. The electrode 2 is placed from the side surface of the container 4 toward the inside of the container 4. The electrode 1 is covered with an insulating material 6. In the analyzer 10, a sample including a target is introduced, for example, into the container 4 such that the sample is in contact with the electrodes 1 and 2. In FIG. 1A and FIG. 1B, the analyzer 10 is a vertical placement type analyzer. However, the analyzer 10 may be, for example, a horizontal placement type.

In FIG. 1A and FIG. 1B, a part of the surface of the electrode 1 is covered with the insulating material 6. However, the insulating material 6 is an optional component. Therefore, the insulating material 6 may be used, and is not necessarily used. Further, the electrodes 1 and 2 are placed on different surfaces of the container 4. However, the positions at which the electrodes 1 and 2 are placed are not particularly limited, and the electrodes 1 and 2 may be placed at any positions.

In FIG. 1A and FIG. 1B, the electrode 1 and the light-transmitting section 3 are in contact with each other. However, for example, the electrode 1 may be placed apart from the light-transmitting section 3. The distance between the electrode 1 and the bottom surface of the container 4 is not particularly limited. The distance may be, for example, from 0 cm to 2 cm, and is preferably from 0 cm to 0.5 cm.

The material of the light-transmitting section 3 is not particularly limited as long as, for example, emission generated by voltage application to the pair of electrodes 1 and 2 can be transmitted through the light-transmitting section 3, and may be appropriately set in accordance with to the wavelength of the emission. Examples of the material of the light-transmitting section 3 include quartz glass, and acrylic resins (for example, polymethyl methacrylate (PMMA)), borosilicate glass, polycarbonate (PC), cycloolefin polymer (COP), methylpentene polymer (TPX (trademark)). The size of the light-transmitting section 3 is not particularly limited as long as, for example, emission generated by voltage application to the pair of electrodes 1, 2 can be transmitted through the light-transmitting section 3.

In FIG. 1A and FIG. 1B, the container 4 has a bottomed cylindrical shape. However, the shape of the container 4 is not limited thereto, and the container 4 may have any shape. The material of the container 4 is not particularly limited, and examples thereof include acrylic resins (for example, polymethyl methacrylate (PMMA)), polypropylene (PP), polyethylene (PE), polyvinyl chloride (PVC), polyethylene terephthalate (PET), and polystyrene (PS). The volume of the container 4 may be, for example, from 0.5 $cm^3$ to 1.5 $cm^3$, or from 0.3 $cm^3$ to 0.5 $cm^3$. In the case where the container 4 has a bottomed cylindrical shape, the diameter of the container 4 may be, for example, from 0.4 cm to 50 cm, and is preferably from 1 cm to 5 cm. The height of the container 4 may be, for example, from 0.3 cm to 50 cm, and is preferably from 0.7 cm to 2 cm.

The light receiving section 5 is not particularly limited, and examples thereof include known optical measuring instruments such as CCD and a spectroscope. The light receiving section 5 may be, for example, a transmission member which transmits the emission to the optical measuring instrument placed outside the analyzer 10. Examples of the transmission member include a transmission path such as an optical fiber.

The method of producing the container 4 is not particularly limited. For example, the container 4 may be produced by obtaining a molded product by injection molding or the like, or by forming a recess in a substrate such as a plate. Other examples of the method of producing the container 4 or the like include, but not particularly limited to, lithography and cutting.

<Inhibitor of Plasma Emission>

An inhibitor of plasma emission derived from a non-target according to the present disclosure (hereinafter, also referred to as an "inhibitor") contains a defoaming agent as a main component, and is used in the analysis method according to the present disclosure. The inhibitor according to the present disclosure contains a defoaming agent, and is used for the analysis method according to the present disclosure. Other constitutions and conditions are not particularly limited. The inhibitor according to the present disclosure is capable of suppressing the plasma emission derived from a non-target in the analysis method according to the present disclosure. Regarding the details of the defoaming agent in the inhibitor according to the present disclosure, reference can be made to the description of the defoaming agent used in the analysis method according to the present disclosure. The details of the analysis method according to the present disclosure in the definition of the inhibitor according to the present disclosure are as previously described.

The term "main component" means a component which has a function of suppressing plasma emission derived from a non-target in the analysis method according to the present disclosure. The inhibitor may consist of a defoaming agent, or may contain an additional component such as an additive, in addition to the defoaming agent.

The form of the inhibitor is not particularly limited, and may be appropriately determined in accordance with the type of the defoaming agent or the like. The form of the inhibitor may be, for example, a solid or a liquid.

The defoaming agent according to the present disclosure may be used for inhibiting plasma emission derived from a non-target in the plasma analysis method according to the present disclosure.

EXAMPLES

Next, Examples will be described. The invention is not limited by the following Examples.

Example 1

It was confirmed that plasma emission derived from a non-target in a sample was suppressed by coexistence of a defoaming agent.

(1) Plasma Spectroscopic Analyzer

As a plasma spectroscopic analyzer, a bottomed cylindrical container formed of transparent PMMA (height: 15 mm.×diameter φ: 10 mm) was provided. At the center of the bottom of the container, quartz glass was placed. An electrode 1 and an electrode 2 were placed in the container. The electrode 1 was placed in a direction perpendicular to the bottom surface of the container. The electrode 1 was placed such that one end of the electrode 1 was in contact with the quartz glass at the bottom of the container. As the electrode 1, a brass rod having a diameter of 0.12 mm was used. The electrode 1 used was configured such that a portion of 0.3 mm in length from the tip was exposed and the remaining portion was insulated. The electrode 2 was placed toward the inside of the container from the side surface of the container in a direction perpendicular to the electrode 1. As the electrode 2, a carbon electrode rod having a diameter of 2.5 mm was used. An optical fiber was placed such that it faced the tip of the electrode 1 with the quartz glass therebetween. As the optical fiber, a single-core optical fiber having a diameter of 400 μm was used. The optical fiber was connected to a concave grating type spectroscope (self-prepared).

(2) Analysis of Mercury

Urine samples were collected from two subjects (A and B), and ethanol was added to each of the urine samples such that each of the urine samples had a final ethanol concentration of 5% by volume. The urine samples containing ethanol were named as Example Samples A and B, and the urine samples not containing ethanol were named as Comparative Example Samples A and B.

400 μL of each of the Samples was introduced into the container of the analyzer. A voltage was applied between the electrode 1 and the electrode 2 such that the electrode 1 served as a cathode and the electrode 2 served as an anode, under the following concentration conditions, whereby mercury was concentrated in the vicinity of the electrode 1.

(Concentration Conditions)
Application cycle: 4 seconds
Non-application duration: 2 seconds
Pulse width: 2 seconds
Duty: 50%
Current while applying a voltage: 20 mA
Current while not applying a voltage: 0 mA
Number of application cycles: 300
Duration of concentration process: 1200 seconds Immediately after the concentration process, a voltage and a current were applied between the electrode 1 and the electrode 2 such that the electrode 1 served as an anode and the electrode 2 served as a cathode, under the following plasma generation conditions, thereby generating plasma. Regarding the plasma emission due to the plasma, emission intensity (count value) was measured at each wavelength. The peak wavelength of plasma emission derived from mercury is approximately 253 nm.

Figure 2A:
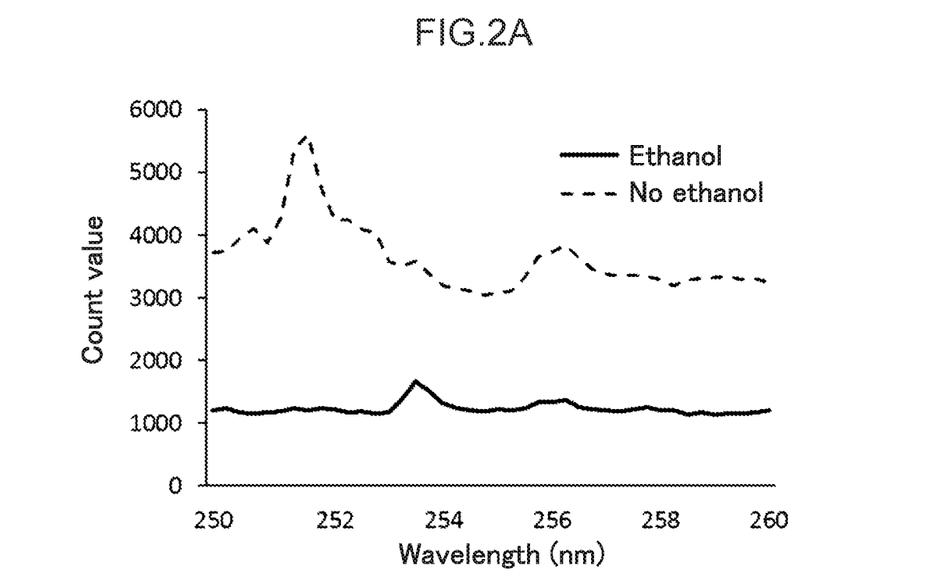
Figure 2B:
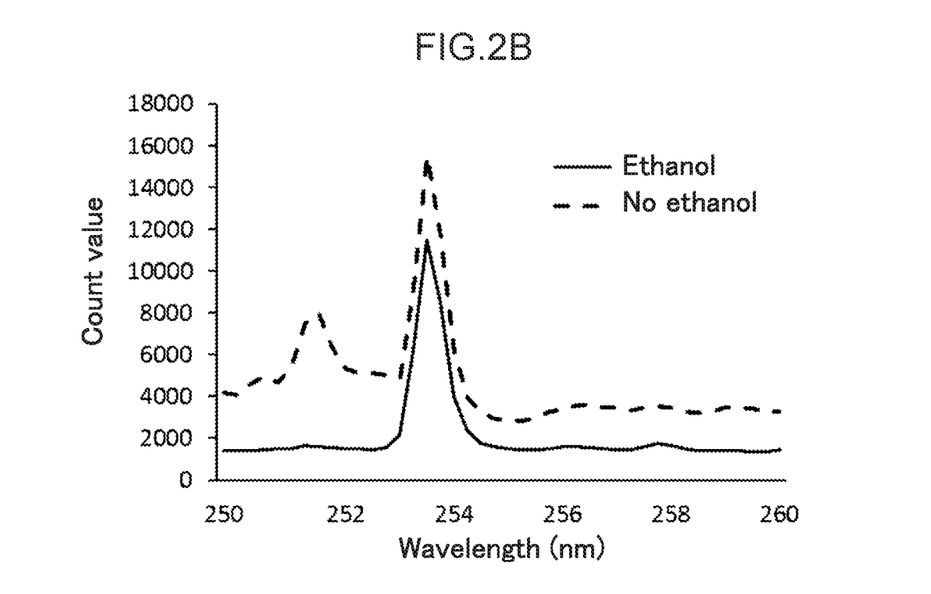

(Plasma Generation Conditions)
Pulse width: 50 μs
Duty: 50%
Voltage value while applying a voltage: 500 V
Voltage value while not applying a voltage: 0 V
Number of application cycles: 25
Duration of plasma generation process: 2.5 msec The results are shown in FIG. 2A and FIG. 2B. FIG. 2A and FIG. 2B are graphs showing a spectrum in the vicinity of a peak of emission derived from mercury. FIG. 2A shows the results of Example Sample A and Comparative Example Sample A of subject A. FIG. 2B shows the results of Example Sample B and Comparative Example Sample B of subject B. In FIG. 2A and FIG. 2B, the horizontal axes represent wavelength, and the vertical axes represent emission intensity (count value). In FIG. 2A and FIG. 2B, the solid lines show the results of the Example Samples, and the dashed lines show the results of the Comparative Example Samples.

As shown in FIG. 2A, in the result of Comparative Example Sample A (dashed line), a clear peak was not observed at a wavelength of plasma emission specific to mercury (approximately 253 nm), and a peak derived from a non-target was observed at a wavelength lower than the above wavelength (approximately 252 nm). On the other hand, in the result (solid line) of Example Sample A, the baseline was lowered; the peak derived from a non-target was not observed; and a peak was observed only at a wavelength specific to mercury. Similar results were obtained in FIG. 2B. In the result of the Comparative Example Sample B (dashed line), a peak was observed at a wavelength specific to mercury. However, a peak derived from a non-target was also observed at another wavelength. On the other hand, in the result of Example Sample B (solid line), a baseline was lowered; a peak derived from a non-target was not observed; and a peak was observed only at a wavelength specific to mercury. These results indicate that the analysis method according to the present disclosure enables suppression of plasma emission derived from a non-target, and enables analysis of mercury, a target, with high sensitivity.

(3) Analysis of Lead

Emission intensity (count value) at each wavelength was measured in the same manner as in Example 1 (2) using the same urine samples as those in Example 1 (2). The peak wavelength of plasma emission derived from lead is approximately 368 nm.

Figure 3A:
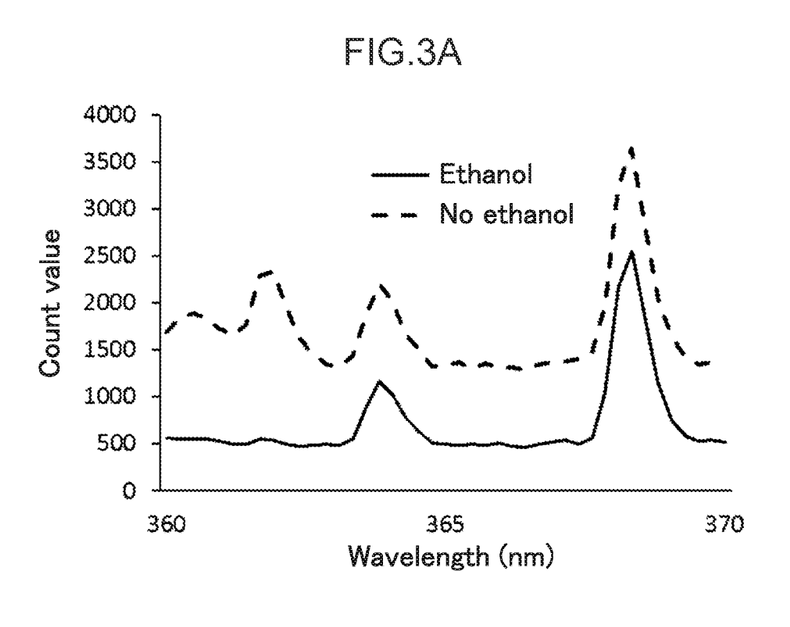
Figure 3B:
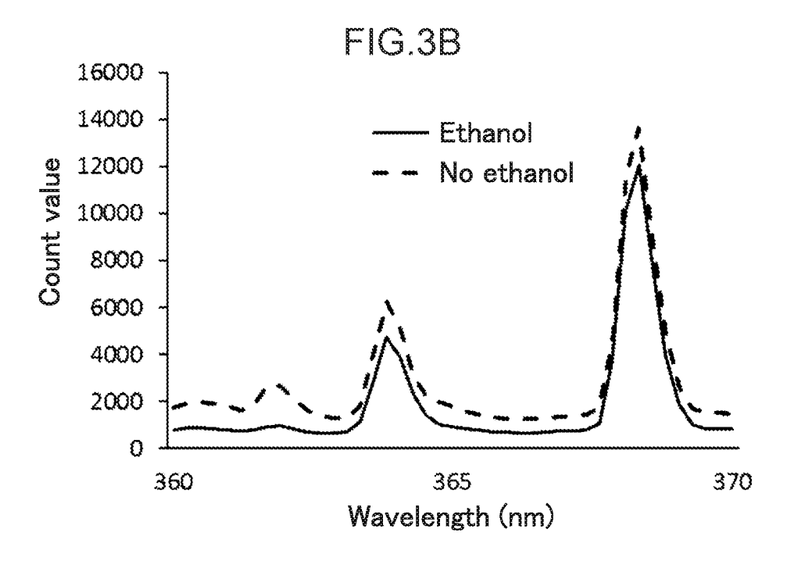

The results are shown in FIG. 3A and FIG. 3B. FIG. 3A and FIG. 3B are graphs showing a spectrum in the vicinity of a peak of emission derived from lead. FIG. 3A shows the results of Example Sample A and Comparative Example Sample A of subject A. FIG. 3B shows the results of Example Sample B and Comparative Example Sample B of subject B. In FIG. 3A and FIG. 3B, the horizontal axes represent wavelength, and the vertical axes represent emission intensity (count value). In FIG. 3A and FIG. 3B, solid lines show the results of the Example Samples, and the dashed lines show the results of Comparative Example Samples.

As shown in FIG. 3A, in the result of Comparative Example Sample A (dashed line), a peak was observed at a wavelength of plasma emission specific to lead (approximately 368 nm). However, peaks derived from non-targets were also observed at other wavelengths (approximately 362 nm and 364 nm). On the other hand, in the result of Example Sample A (solid line), the baseline was lowered; a peak derived from a non-target at a wavelength of approximately 362 nm disappeared; a peak derived from a non-target in the vicinity of a wavelength of 364 nm was lowered; and a peak having a wavelength specific to lead became clear. Similar results were obtained in FIG. 3B. In the result of the Comparative Example Sample B (dashed line), a peak was observed at a wavelength specific to lead. However, peaks derived from non-targets were also observed at other wavelengths. On the other hand, in the result of Example Sample B (solid line), the baseline was lowered; a peak derived from a non-target in the vicinity of a wavelength of 362 nm disappeared; a peak derived from a non-target in the vicinity of a wavelength of 364 nm was lowered; and a peak having a wavelength specific to lead became clear. These results indicate that the analysis method according to the present disclosure enables suppression of plasma emission derived from a non-target and enables analysis of lead, a target, with high sensitivity.

Example 2

Changing the concentration of a defoaming agent, it was confirmed that plasma emission derived from a non-target in a sample was suppressed.

(1) Analysis of Mercury

Mercury in urine samples was analyzed in the same manner as in Example 1 (2) except that, to urine samples collected from the subjects, ethanol was added such that the urine samples had final concentrations of 0% by volume, 5% by volume, and 12.5% by volume.

Figure 4:
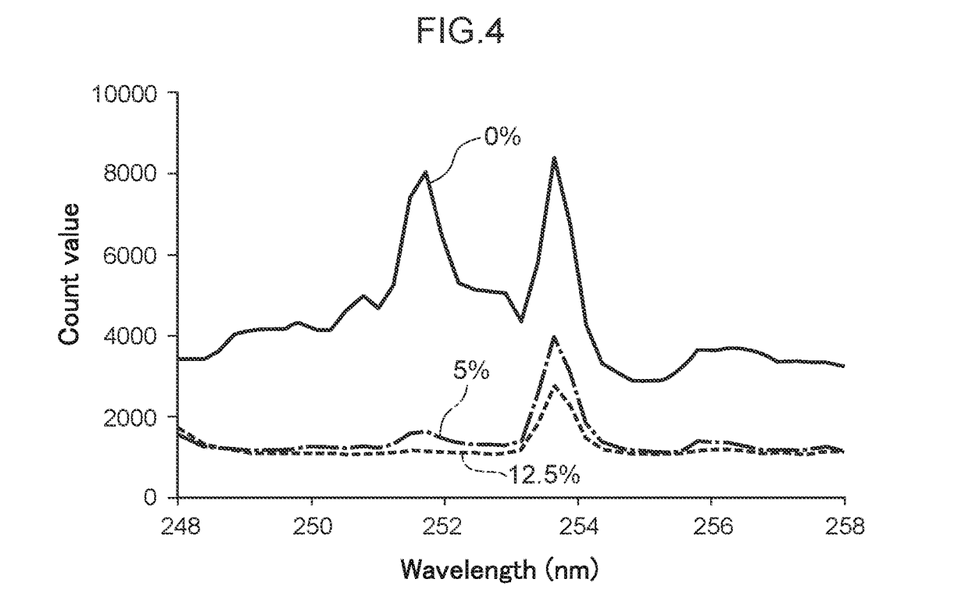
FIG. 4 is a graph showing a spectrum in the vicinity of a peak of emission derived from mercury in urine samples having different concentrations of ethanol added in Example 2.

The results are shown in FIG. 4. FIG. 4 is a graph showing a spectrum in the vicinity of a peak of emission derived from mercury in each of the urine samples having different ethanol concentrations. In FIG. 4, the horizontal axis represents wavelength, and the vertical axis represents emission intensity (count value). As shown in FIG. 4, in the sample not containing ethanol (0% by volume), a peak was observed at a wavelength specific to mercury (approximately 253 nm). However, a peak derived from a non-target was also observed at another wavelength (approximately 252 nm). On the other hand, in the sample containing ethanol, the baseline was lowered at both ethanol concentrations; a peak derived from a non-target almost disappeared; and a peak was confirmed only at a wavelength specific to mercury.

(2) Measurement of Lead Peak

Lead in urine samples was analyzed in the same manner as in Example 2 (1) using the same urine samples as those in Example 2 (1).

Figure 5:
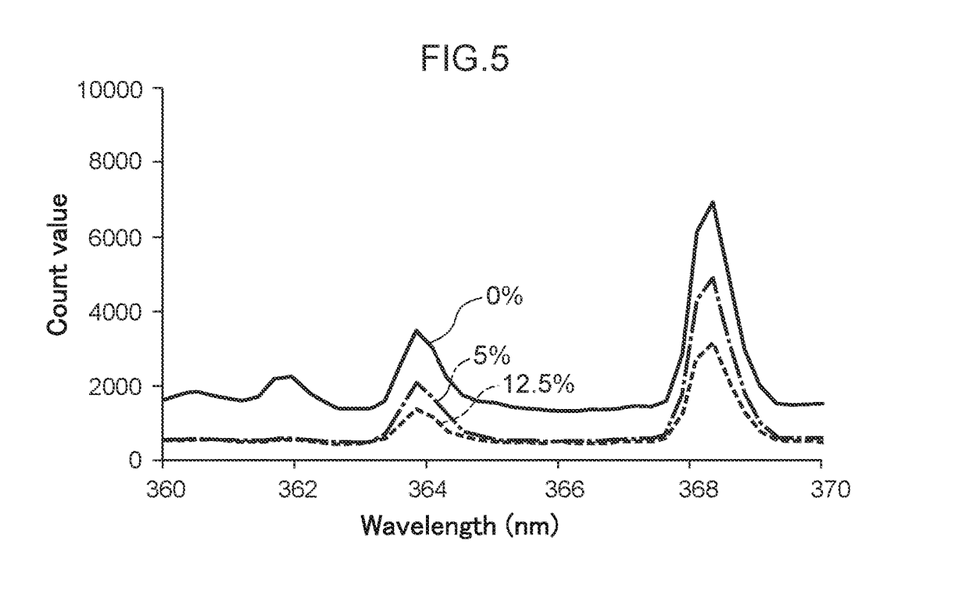
FIG. 5 is a graph showing a spectrum in the vicinity of a peak of emission derived from lead in urine samples having different concentrations of ethanol added in Example 2.

The results are shown in FIG. 5. FIG. 5 is a graph showing a spectrum in the vicinity of a peak of emission derived from lead in each of the urine samples having different ethanol concentrations. In FIG. 5, the horizontal axis represents wavelength, and the vertical axis represents emission intensity (count value). As shown in FIG. 5, in the sample not containing ethanol (0% by volume), a peak was observed at a wavelength specific to lead (approximately 368 nm). However, peaks derived from non-targets were also observed at other wavelengths (approximately 362 nm and 364 nm). On the other hand, in the samples containing ethanol, the baseline was lowered at both ethanol concentrations; the peak derived from a non-target in the vicinity of the wavelength of 362 nm disappeared; the peak derived from a non-target in the vicinity of the wavelength of 364 nm decreased; and the peak at the wavelength specific to lead became clear.

In both Examples 2 (1) and (2), emissions derived from non-targets were sufficiently suppressed under the condition of the ethanol concentration of 12.5% by volume, and peaks of the emissions derived from the targets were maintained at approximately one-half of the peaks of the Comparative Example Samples. These results indicate that sufficient S/N ratio is maintained. Furthermore, when the ethanol concentration was 5% by volume, emissions derived from non-targets were suppressed, and peaks of emission derived from the targets were maintained at approximately ¾ of the peaks in the Comparative Example Samples. These results indicate that higher S/N ratio is obtained.

Example 3

It was confirmed that plasma emission derived from a non-target in a sample was suppressed by using various defoaming agents.

Mercury and lead in urine samples were analyzed in the same manner as in Example 1 (2) except that, as a defoaming agent, ethanol, methanol, butanol, isopropanol, acetone, SN DEFORMER 777 (San Nopco), and TRITON (trademark) X-100 were added respectively to urine samples collected from the subjects such that the urine samples had a final concentrations of 5% by volume, or no defoaming agent was added (0% by volume). The urine samples containing no defoaming agent were used as Comparative Example Samples.

Figure 6A:
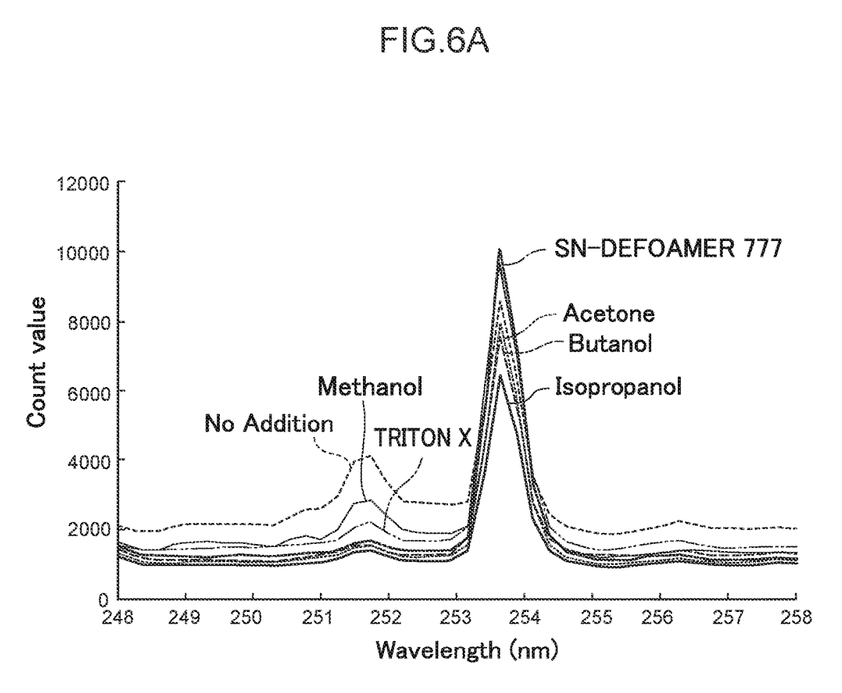
FIG. 6A is a graph showing a spectrum in the vicinity of a peak of emission derived from mercury in urine samples to which different defoaming agents are added in Example 3.
Figure 6B:
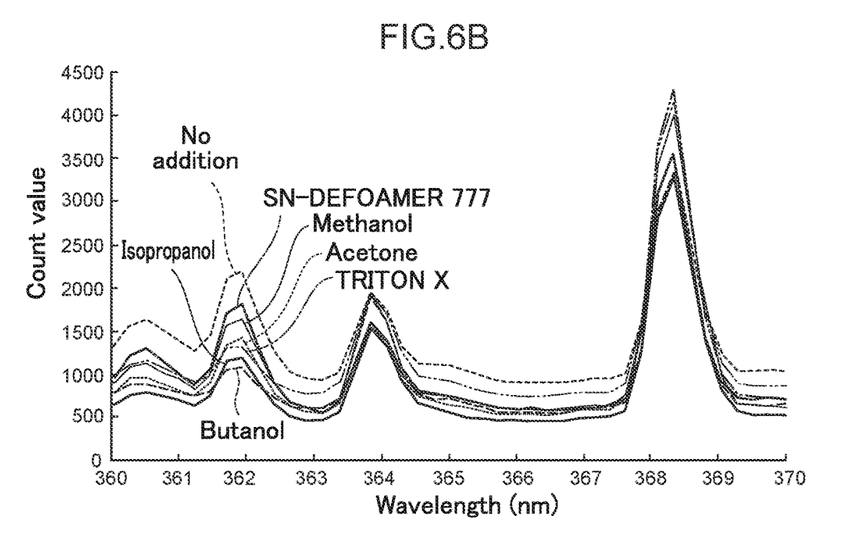
FIG. 6B is a graph showing a spectrum in the vicinity of a peak of emission derived from lead in urine samples to which different defoaming agents were added in Example 3.

The results are shown in FIG. 6A and FIG. 6B. FIG. 6A is a graph showing a spectrum in the vicinity of a peak of emission derived from mercury in urine samples to which different defoaming agents were added. FIG. 6B is a graph showing a spectrum in the vicinity of a peak of emission derived from lead in urine samples to which different defoaming agents were added. In FIG. 6A and FIG. 6B, the horizontal axes represent wavelength, and the vertical axes represent emission intensity (count value). As shown in FIG. 6A, in the case of the Comparative Example Sample, a peak was observed at a wavelength of plasma emission specific to mercury (approximately 253 nm). However, a peak derived from a non-target was also observed at another wavelength (approximately 251.6 nm). On the other hand, when any of the defoaming agents was added, the baseline was lowered; the peak derived from the non-target was lowered; and the peak at the wavelength specific to mercury became clear. In particular, when butanol, isopropanol, acetone, or SN DEFORMER 777 was added, the peak derived from the non-target almost disappeared. As shown in FIG. 6B, in the case of the Comparative Example Sample, a peak was observed at a wavelength of plasma emission specific to lead (approximately 368 nm). However peaks derived from non-targets were also observed at other wavelengths (approximately 360.4 nm, 362 nm, and 364 nm). On the other hand, when any of the defoaming agents was added, the baseline was lowered; the peaks derived from the non-targets were lowered; and the peak at the wavelength specific to lead became clear.

Reference Example

It was confirmed that the addition of distilled water does not suppress plasma emission derived from a non-target in a sample.

In order to confirm whether or not the occurrence of emission peaks other than a target were due to the viscosity of the sample, urine samples were diluted with distilled water, and its influence on the emission peaks other than that of the target was examined. Specifically, mercury and lead in urine samples were analyzed in the same manner as in Example 1 (2) except that distilled water was added, or not added (0% by volume), to the urine samples collected from the subjects, in place of a defoaming agent, such that the urine samples had final concentrations of the distilled water at 25% by volume.

Figure 7A:
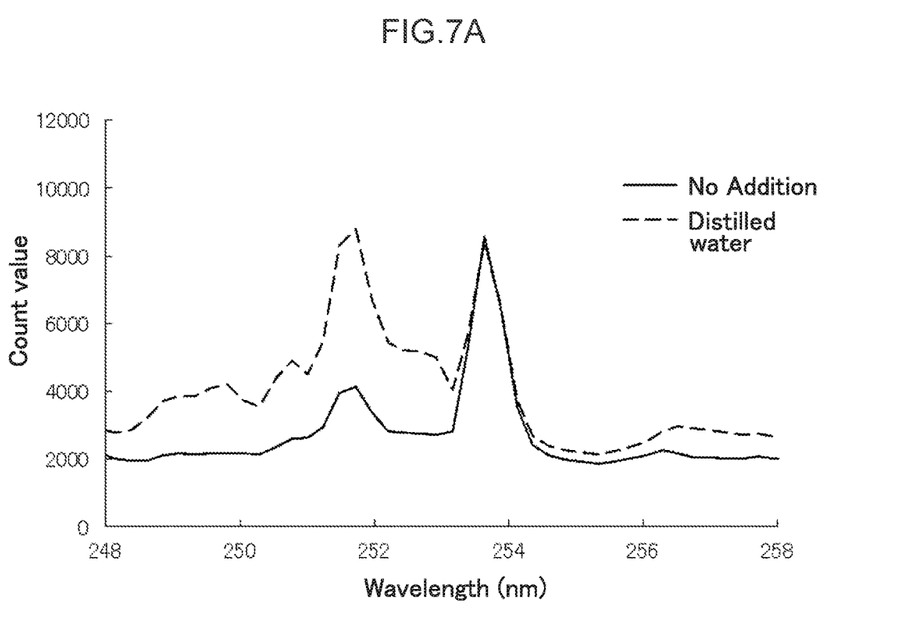
FIG. 7A is a graph showing a spectrum in the vicinity of a peak of emission derived from mercury in a urine sample to which distilled water was added in the Reference Example.
Figure 7B:
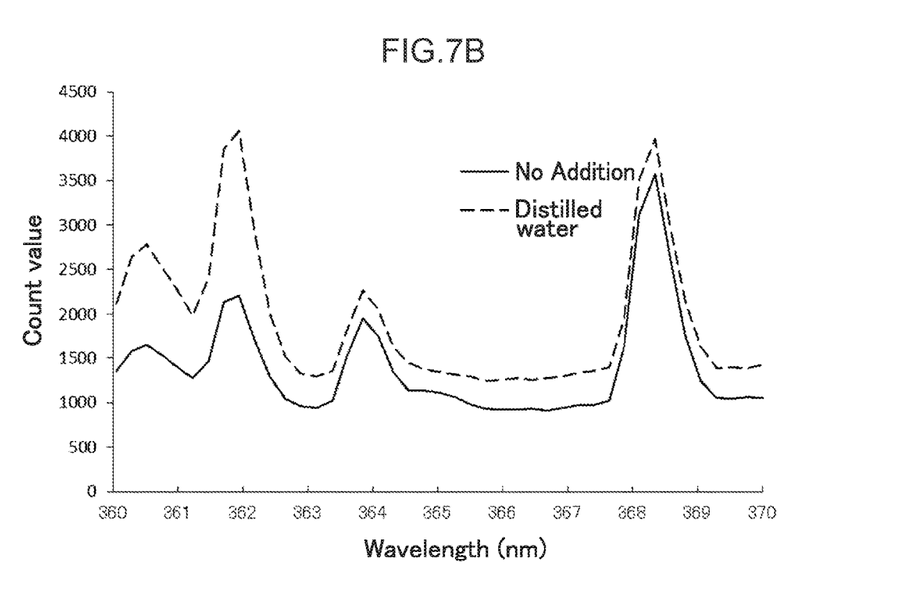
FIG. 7B is a graph showing a spectrum in the vicinity of a peak of emission derived from lead in a urine sample to which distilled water was added in the Reference Example.

The results are shown in FIG. 7A and FIG. 7B. FIG. 7A is a graph showing a spectrum in the vicinity of a peak of emission derived from mercury in a urine sample to which distilled water was added. FIG. 7B a graph showing a spectrum in the vicinity of a peak of emission derived from lead in a urine sample to which distilled water was added. In FIG. 7A and FIG. 7B, the horizontal axes represent wavelength, and the vertical axes represent emission intensity (count value). As shown in FIG. 7A, in the case of the sample to which distilled water was not added (solid line), as with the result of the Comparative Example Sample in Example 3, a peak was observed at a wavelength of plasma emission specific to mercury (approximately 253 nm), and a peak derived from a non-target was also observed at another wavelength (approximately 251.6 nm). On the other hand, in the sample to which distilled water was added, unlike the case where defoaming agents were added in Example 3, the baseline moved upward, and the peak derived from the non-target was heightened. As shown in FIG. 7B, in the case of the sample containing no distilled water (solid line), as with the result of the Comparative Example Sample in Example 3, a peak was observed at a wavelength of plasma emission specific to lead (approximately 368 nm), and peaks derived from non-targets were also observed at other wavelengths (approximately 360.4 nm, 362 nm, and 364 nm). On the other hand, in the sample containing distilled water, unlike the case where defoaming agents were added in Example 3, the baseline moved upward, and the peaks derived from the non-targets were heightened. These results indicate that occurrences of peaks of emission other than a target are not due to the viscosity of the sample.

While the invention has been described above with reference to embodiments and Examples, the invention is not limited to the above-described embodiments and Examples. To the configuration and details of the invention, various changes that can be understood by those skilled in the art may be made without departing from the scope of the invention.

The plasma spectroscopic analysis method according to the present disclosure is capable of suppressing plasma emission derived from a non-target without, for example, removing the non-target by filtering the sample. Therefore, for example, the sample can be analyzed with high sensitivity without changing the concentration or the like of the target in the sample. Accordingly, the plasma spectroscopic analysis method according to the present disclosure is extremely useful for, for example, analysis of elements or the like using the plasma emission.

What is claimed is:

1. A plasma spectroscopic analysis method comprising:
   a concentration process of applying a first voltage to a pair of electrodes in a sample, thereby concentrating a target in the sample in the vicinity of one of the pair of electrodes in the sample;
   a plasma generation process of generating plasma in the vicinity of the one of the pair of electrodes in the sample by applying a second voltage to the pair of electrodes;
   a detection process of detecting emission of the target generated by the plasma; and
   an addition process of adding a defoaming agent to the sample before the plasma generation process.

2. The plasma spectroscopic analysis method according to claim 1, wherein, in the concentration process, a current between the pair of electrodes while applying the voltage is constant.

3. The plasma spectroscopic analysis method according to claim 2, wherein:
   the concentration process includes a voltage application period in which a voltage is applied to the pair of electrodes and a voltage non-application period in which a voltage is not applied to the pair of electrodes, and
   in the voltage application period, the current between the pair of electrodes while applying the voltage is constant.

4. The plasma spectroscopic analysis method according to claim 3, wherein, in the concentration process, when a cycle of one voltage application period and one voltage non-application period is defined as a single set, a duration of the single set is 0.25 seconds or more.

5. The plasma spectroscopic analysis method according to claim 3, wherein, in the concentration process, when a cycle of one voltage application period and one voltage non-application period is defined as a single set, a duration of the voltage non-application period in a duration of the single set is 0.125 seconds or longer.

6. The plasma spectroscopic analysis method according to claim 3, wherein, in the concentration process, when a cycle of one voltage application period and one voltage non-application period is defined as a single set, a ratio of a duration of the voltage application period to the duration of the single set is from 1% to 99%.

7. The plasma spectroscopic analysis method according to claim 1, wherein, in the concentration process, a current value between the pair of electrodes while applying the voltage is from 0.01 mA to 200 mA.

8. The plasma spectroscopic analysis method according to claim 1, wherein:
   each of the pair of electrodes has a different area of contact with the sample, and
   of the pair of electrodes, an electrode having a smaller area of contact with the sample is the one of the pair of electrodes, and is an electrode for analyzing the target by detection of the emission.

9. The plasma spectroscopic analysis method according to claim 1, wherein the defoaming agent is at least one selected from the group consisting of an alcohol compound, a surfactant, and a ketone compound.

10. The plasma spectroscopic analysis method according to claim 9, wherein:
    the defoaming agent is an alcohol compound, and
    the alcohol compound is at least one selected from the group consisting of methanol, ethanol, isopropanol, and butanol.

11. The plasma spectroscopic analysis method according to claim 9, wherein:
    the defoaming agent is a surfactant, and
    the surfactant is at least one selected from the group consisting of an oil-based surfactant, an emulsion-based surfactant, and a polyether-based surfactant.

12. The plasma spectroscopic analysis method according to claim 1, wherein a concentration of the defoaming agent in the sample is within a range of from 0.025% by volume to 12.5% by volume.

13. The plasma spectroscopic analysis method according to claim 1, wherein the voltage applied in the plasma generation process is higher than the voltage applied in the concentration process.

14. The plasma spectroscopic analysis method according to claim 1, wherein the voltage applied in the concentration process is 1 mV or higher.

15. The plasma spectroscopic analysis method according to claim 1, wherein the voltage applied in the plasma generation process is 10 V or higher.

16. The plasma spectroscopic analysis method according to claim 1, wherein the target is a metal.

17. The plasma spectroscopic analysis method according to claim 16, wherein the metal is at least one metal selected from the group consisting of aluminum, antimony, arsenic, barium, beryllium, bismuth, cadmium, cesium, gadolinium, lead, mercury, nickel, palladium, platinum, tellurium, thallium, thorium, tin, tungsten, and uranium.

18. The plasma spectroscopic analysis method according to claim 1, wherein:
    the pair of electrodes is placed in a container;
    the container comprises a light-transmitting section; and
    a light receiving section, which is capable of receiving plasma emission derived from the target through the light-transmitting section, is placed outside the container.

19. The plasma spectroscopic analysis method according to claim 1, further comprising using the defoaming agent to inhibit plasma emission derived from a non-target.

* * * * *